United States Patent [19]

Adkinson

[11] Patent Number: 5,211,961
[45] Date of Patent: May 18, 1993

[54] COMPOSITION, AND METHOD, FOR PREMILKING UDDER HYGIENE

[75] Inventor: Robert W. Adkinson, Baton Rouge, La.

[73] Assignee: Louisiana State University Board of Supervisors, Baton Rouge, La.

[21] Appl. No.: 862,429

[22] Filed: Apr. 2, 1992

Related U.S. Application Data

[63] Continuation-in-part of Ser. No. 575,090, Aug. 30, 1990, abandoned.

[51] Int. Cl.$^5$ ............ A01N 39/00; A01N 59/08; A01N 59/22; A01N 37/52
[52] U.S. Cl. ........................ 424/616; 424/661; 424/667; 514/634; 514/635; 514/642; 514/944
[58] Field of Search ............ 424/616, 661, 667; 514/634, 635, 642, 944

[56] References Cited

U.S. PATENT DOCUMENTS 3,993,777  11/1976  Caughman et al. .............. 514/642
4,113,854   9/1978  Andrews et al. ................. 424/81

Primary Examiner—Frederick E. Waddell
Assistant Examiner—K. Weddington
Attorney, Agent, or Firm—Llewellyn A. Proctor

[57] ABSTRACT

A gel composition for cleaning and sanitizing the teats and udder of an agricultural animal for machine milking. Residual surface water, a source of milk contamination and mastitis, is eliminated from the teats and udder by use of the gel composition. The composition is constituted of water, a germicide added to the water in concentration sufficient to kill environmental bacteria which cause mastitis, and an aqueous gelling agent added to the water in concentration sufficient to form a palpable jelly-like mass, or gel. The composition preferably also includes a soap, detergent or other agent for the reduction of surface tension, and a skin softener and moisturizer. It preferably also contains a coloring agent. In application, the composition is applied to the teats and udder to soften and emulsify the particulate foreign matter, and kill the bacteria which cause environmental mastitis, without the separation therefrom of a separate liquid phase. The composition is then wiped from the teats, the teats cleaned, and the milking machine attached to the clean teats. The composition, when applied, adheres to the udder surface and teats until wiped away throughout which period water does not separate from the gel, drain, or drip from the udder surface and teats.

28 Claims, No Drawings

COMPOSITION, AND METHOD, FOR PREMILKING UDDER HYGIENE

RELATED APPLICATIONS

This is a continuation-in-part of application Ser. No. 575,090, filed Aug. 30, 1990, now abandoned.

FIELD OF THE INVENTION

This invention relates to a composition, and method, for premilking udder hygiene. In particular, it relates to a composition, and method, for preparing the udders and teats of agricultural animals for milking to provide more sanitary conditions.

BACKGROUND

Mastitis, an infectious disease of the udder, is the most costly disease in U.S. animal agriculture. The condition is widespread among dairy cattle and exacts a high toll in lowered milk yield and reduced milk quality due to changes in the composition of the milk. Mastitis and mastitis control are complex problems, but good premilking udder hygiene has been recognized as a basic factor in the reduction and prevention of mastitis. Milking machines, the use of separate milking parlors, and pipeline milking have improved the sanitary conditions under which milk is handled on the farm. The milking parlor is generally used when the cows are not housed in a stanchion barn, but are allowed to run loose. The cows are brought into the parlor, and their flanks, udders and teats are washed and dried before attaching the milking machines. The double chamber teat cup provides the interface between the cow and the milking machine. The double chamber teat cup with a pulsating outer chamber is employed in practically all milking machines in use today. The unit is constituted of four teat cup shells, liners and a clawpiece (manifold). A partial vacuum supplied by a pulsator provides an intermittent opening and closing of the liner. When, during the milking phase, vacuum is applied to both the inner and outer chambers, the liner is open, and milk is withdrawn from the teat. When, during the resting phase, air is admitted to the outer chamber only, the liner closes upon the teat, and the flow of milk is interrupted. The milking machine has been recognized along with the milker's hands and udder washing materials as part of the environment which can affect the incidence, prevalence and severity of mastitis.

Dairymen use many methods of cleaning cow's udders and teats prior to milking, most of which involve washing away manure, mud and other environmental dirt contaminants with water. Commonly, the udder and teats are washed via use of a spray nozzle and each teat then individually massaged and dried with paper towels. Water is inevitably trapped by hair on the udders and flanks and drains downwardly during milking. The water collects on top of the inflation of the teat cup that surrounds a teat and is pulled by vacuum into the space between the inflation and the teat by the milking action. Subsequently, it ends up in the milk. Moreover, an abrupt reduction in vacuum can cause movement of air toward the teat end, and contaminated droplets may impact the teat end. The impact may also force bacteria in the teat duct into the teat cistern. Thus, the abrupt loss of vacuum caused by liner slips, machine drop-off or take-off without prior vacuum shut off are the types of positive variations which can force the contaminated water into the teat, an effect which can cause mastitis.

No matter how well the cow has been washed, water from the draining surface of the udder and flanks is contaminated with bacteria, the contaminated water collecting on the top of the inflation to be pulled by vacuum into the space between the inflation and the teat by the milking action, and sharp reductions in vacuum, these conditions causing the contaminated water to find its way into the milk to reduce milk quality and into the teats to increase the incidence of mastitis. Many farmers and researchers have experimented with premilking sanitizing teat dips and wash solutions. Some improvement in the quality of the milk has been made, it is believed, by the use of a teat dip subsequent to water spraying and cleaning the udder and teats, followed by attachment of the milking machine. In most premilking udder hygiene practices, however, sanitizing washes and teat dips have produced little or no benefit. In conventional practice, water continues the cleaner of choice for premilking udder hygiene; and, teat dips are applied after the milking phase has been completed. In any event, much of the problem, it is now recognized, is due to the contamination caused by the excess water which drains from the cow's flank, teats and udder during milking. Thus, there exists a profound need for improved, premilking udder hygiene.

OBJECTS

It is, accordingly, a primary objective of the present invention to provide this, and other needs.

In particular, it is an object to provide a novel composition, and method employing such composition, for preparing the udders and teats of agricultural animals for milking.

A further and more specific object is to provide, for cleaning the surface of the cow's udder and teats, a germicidal composition which, after application, does not drain from the surface to which it is applied; thus avoiding this type of contamination.

THE INVENTION

These objects and others are achieved in accordance with the present invention:

a composition, or cleaner, useful for improving the premilking udder hygiene in agricultural animals which comprises an admixture of (a) water, (b) a germicide in concentration sufficient to destroy environmental bacteria that cause mastitis, and (c) an aqueous gelling agent in concentration sufficient to coagulate and gel with the water. The gelling agent is dissolved in the water, with the germicide, in amount sufficient to form a tactile palpable plastic mass, or jelly. The composition is dispensed, wiped, brushed, or otherwise applied, upon the surface of the udder and teats, e.g., by hand, to adhere to the surface to which it is applied without separation of the retained water. The composition is wiped away after it has softened and emulsified the particulate matter on the surface to which it is applied, and has remained in place for a sufficient time for the germicide to kill a preponderance of the environmental organisms on the surface of the udder and teats. The composition, from the time it is applied to the time it is wiped away to cleanse the surface to which it is applied, retains the water component without draining or dripping from the surface to which it is applied. In forming the composition, the gelling agent is added to the water, and germicide, in an amount sufficient to provide an apparent viscosity ranging from about 1,500 Cp (centipoises) to about 2,000,000 Cp, preferably from about 3,000 Cp to about 150,000 Cp, as measured at 25° C. with a Brookfield LVT Viscometer equipped with a helipath stand using T-bar spindles A, B, C, D, E and F at rotational speeds up to 6 rpm (revolutions per minute), tested as recommended by the manufacturer of the instrument. A gel of this consistency forms a palpable plastic jelly-like mass of capacity adequate to soften and emulsify the particulate matter, i.e., manure, mud or other dirt, and sanitize the udder and teats to which the composition is applied without the separation therefrom of a separate liquid phase. The preponderance of the composition can then be wiped away to clean the teats, and the milking machine the attached. Accordingly, there is no separate contaminated liquid phase to drip or drain from the surface of the udder and teats to escape into the space between the inflation of a teat cup of the milking machine and the teat of the animal to contaminate milk, or impact teat ends, and hence the hazard of mastitis from this source is eliminated.

The gel, after its formation, is a pseudo-plastic mass, or jelly, within which the water is retained. The composition is a non-Newtonian fluid having an apparent viscosity and rate of shear which changes with changing shear stress; the shear stress being related to spindle speed (revolutions per minute) while the rate of shear is related to the measured torque and spindle length as measured by rotation of spindles at different speeds within the material. The composition of this invention, is thus one formed by adding sufficient of a gelling agent to the water to form a gel calculated as having an apparent viscosity ranging between about 1,500 Cp and about 2,000,000 Cp, preferably from about 3,000 Cp to about 150,000 Cp. A composition of this viscosity has sufficient physical texture and cohesiveness sufficiently high that it can be massaged on the udder and teats of an animal to stimulate milk ejection and soften stubborn particulate solids, and subsequently wiped away, without any separation of water therefrom. No water drains, or drips from the surface of the udder and teats under gravity conditions, as is normal after conventional washing procedures. The test for the measurement of viscosity, pursuant to the practice of this invention, is described in *Fundamentals of Food Engineering*, By Stanley Charn (1978), AVI Publishing Company, Inc., Westport, Conn. The instrument used is the Brookfield Digital Viscometer Model DV-II, No. M/85-160-G, Brookfield Engineering Laboratories, Inc., Stoughton, Mass. 02072.

Germicides that are found useful in destroying environmental bacteria that cause bovine mastitis includes generally, salts of chlorhexadine, e.g., acetate salts, gluconate salts and the like; hypochlorites, e.g., sodium hypochlorite ("chlorine bleach"); iodine, e.g., iodine in the form of iodophor, peroxides, e.g., $H_2O_2$, quaternary ammonium compounds, and the like. In general, the germicide is added to the water, and dissolved or otherwise dispersed therein, in concentration ranging from about 0.001 percent to about 4 percent, preferably from about 0.10 percent to about 0.75 percent, based on the total weight of the composition, dependent on the nature, toxicity and the time of contact of the germicide with the treated teats and udder. The aqueous gelling agent is one which, when added to the water, or water and germicide, will coagulate and gel therewith to create a palpable jelly-like mass which can be readily spread or applied upon the teats and udder of an agricultural animal for the time required for the treatment without formation of a separate liquid phase, as generally manifested after conventional wash techniques where water drains, and drips from udder and teat surfaces via gravity separation. Aqueous gelling agents which are found suitable for this purpose include cellulose ethers, or cellulose derivatives, which are particularly preferred, e.g., methyl cellulose, carboxy methyl cellulose, carboxy ethyl cellulose, hydroxypropylmethyl cellulose, and the like; polysaccharides, suitably water soluble plant and tree extrudates, e.g., acadia gum, karaya gum; marine plant extracts, e.g., agar-agar, algin, carageenin; seed extracts e.g., carob bean gum, guar gum; fruit and vegetable extract, e.g., pectin; polyacrylamide, e.g., gelatin, and the like. The aqueous gelling agent, in all embodiments, is added to the water in amount sufficient to form a palpable jelly-like mass which, when applied to the udder and teats of an animal will soften and emulsify the particulate matter, i.e., manure, mud and other dirt, and sanitize the udder and teats to which the composition is applied without formation of a separate liquid phase. The gelling agent is added in amount sufficient to provide an apparent viscosity ranging from about 1,500 Cp to about 2,000,000 Cp, preferably from about 3,000 Cp to about 150,000 Cp, supra, this generally requiring up to about 10 percent, more generally and preferably from about 0.5 percent to about 5 percent of the aqueous gelling agent, based on the total weight of the composition, dependent on the nature of the gelling agent. The composition, in its preferred form, will contain sufficient of the germicide, when spread on the udder and teats of an agricultural animal, to destroy a preponderance of the environmental bacteria that cause mastitis within a contact time ranging between about 10 seconds and 90 seconds, preferably about 15 seconds to about 30 seconds. After this period of treatment, the composition can be removed from the teats, and udder, by wiping with paper towels. During the period of treatment the composition will remain a palpable jelly-like mass, without forming a separate liquid phase. The water component of the composition will be retained throughout the period of treatment, and will not drain or drip from the surface to which the composition is applied.

In its more preferred form the composition will further include [besides components (a), (b) and (c)] (d) an agent for the reduction of the surface tension of the water to enhance the wetting and cleaning properties of the composition, and (e) a skin softener and moisturizer for the protection of the skin surface of the teats and udder of the agricultural animal to which the composition is applied.

Agents useful for reducing the surface tension of water are well known and include soaps, detergents, and surfactants of a wide variety of classes, and subclasses. The older surface active agents are the soaps, i.e., the alkali metal salts of organic acids, e.g., the sodium or potassium salt of an animal or vegetable fat, such as sodium palmitate. The detergents and surfactants are similar to soaps, the older surface active agents, in that they are polar and contain a hydrocarbon chain of variable length and a solubilizing group. The hydrocarbon portion of the molecule, depending on its length, is more or less orhydrophobic or water-repelling. The solubilizing group, on the other hand, is hydrophilic or water-attracting. The combination of these two groups provides a molecule which is active at interfaces by effecting reduction of the surface tension.

These classes of compounds are exemplified generally by, e.g., a disodium salt of a sulfated fatty acid, glyceryloleate, sodium cetyl sulfate, sodium aryl sulfonate, and the like. The surface active agent is generally used in concentration ranging from about 0.01 percent to about 5 percent, preferably from about 2 percent to about 5 percent, based on the total weight of the composition.

The skin softener and moisturizer is used to condition, protect and provide for the comfort of the agricultural animal when it is returned to its daily routine. A wide variety of water soluble compounds of this type are known for cosmetic use exemplary of which are lanolin, glycerine, laurel sulfate and the like. Generally, the skin conditioner is employed in concentration ranging from about 0.01 percent to about 10 percent, preferably from about 0.1 percent to about 5 percent, based on the total weight of the composition.

(f) A coloring agent is not essential, but preferably is also added to enhance the color of the composition. Conventional coloring agents, both natural and synthetic, as presently approved for use in foods, drugs and cosmetics are generally satisfactory. The Food and Agriculture Organization and the World Health Organization have published chemical specifications for a number of colors. See, e.g., Joint FAO/WHO Expert Committee on Food Additives, "Specifications for the Identity and Purity and Toxicological Evaluation of Food Colors, in Press 1966;" and Specifications for Identity and Purity of Food Additives, Vol II. Food Colors, Food and Agriculture Organization and the World Health Organization, Rome, 1963. A description of useful food, drug and cosmetics coloring agents is given in 21 CFR 70.

The composition of this invention is applied to the surface of the udder and teats of the agricultural animal by any suitable means, suitably, e.g., by brushing, daubing, rubbing, or wiping; preferably by hand wiping and massaging. The composition, preferably the composition which includes all of components (a), (b), (c), (d) and (e), supra, and generally also a coloring agent (f), is applied to the teats and udder by hand wiping, rubbing or massaging. The composition is allowed to remain on the teats for a time sufficient to soften, emulsify and suspend dirt and other particulates, and kill the environmental microorganisms which produce bovine mastitis, the most common of which are known to include several types of streptococie and the coliform group. Some of these organisms are present in the feces of the animal, and others are common in soil and plant material; sources of contamination which cannot be eliminated from the animal's environment. The composition is allowed to remain on the teats for a period of time ranging between about 10 seconds and 90 seconds, preferably for a period of from about 15 seconds to about 30 seconds. Each teat and part of the udder, is then wiped with a paper towel to remove the composition and clean the surface. A teat cup of the milking machine is then applied to each of the cleaned, wiped teats.

The following examples, and comparative demonstrations, are exemplary of the high degree of effectiveness of the compositions of this invention, and method, for cleaning the teats of agricultural animals for machine milking at more sanitary conditions. The data shows the greater effectiveness of the compositions of this invention for cleaning and sanitizing heavily soiled teats as contrasted with conventional methods which, as contrasted with the compositions of this invention, leaves the teats and udders wet. Wet udders and teats are shown to lower milk quality, and increase the incidence of bovine mastitis because water drains from the wet udders and teats during milking.

EXAMPLES

Three methods of preparing cows for machine milking were conducted, one to illustrate the present invention and two for comparative purposes. Thirty Holstein cows were thus divided into three groups of ten each and randomly assigned for treatment to one of the three premilking procedures. Two days before the start of the data collection, quarter milk samples on the entire herd were cultured to identify any pathogens present. One cow was removed from the study due to a *Staphylococcus aureus* infection, this cow having been infected before the study began. All cows used in the study were free of infection.

The housing was identical for all cows regardless of treatment. Cows were housed in a loafing barn, cleaned daily; though cows were generally dirty. The cows were milked twice a day starting at 3:00 a.m. and 2:30 p.m., respectively. Milking parlor was a side opening parlor with eight stalls in a double-four arrangement. A weigh jar was present in each stall. Machines were removed by hand. Individual cow milk production was recorded at each milking. Other management factors like feeding, reproduction, health care, etc. were uniform for all cows in the study.

Prior to each treatment, a strip check was made of a cow for abnormalities. Prior to attaching the cluster of the milking machine, subsequent to the treatment, each teat was wiped thoroughly with a single use paper towel. Sometimes more than one paper towel was used per cow, but never more than one cow per paper towel to avoid possible contamination. The treatments were continued over a period of ten weeks. The treatments consisted of (1) premilking cleaning of teats using a cleaning gel of this invention applied by hand, massaging each teat using a minimum of 3 to 4 vertical motions up and down the sides of the teat, and 1 or 2 horizontal motions across the teat ends, and left on the teats for approximately 30 seconds and then wiping the gel from the teats with separate paper towels for each cow prior to attachment of the teat cups of the milking machine to the teats, this being referred to hereafter as the GEL method; (2) premilking cleaning of teats with a spray of water using a water hose and wiping with hands, massaging each teat using a minimum of 3 to 4 vertical motions up and down the sides of the teat, and 1 or 2 horizontal motions across the teat ends, followed by drying the teats with separate paper towels for each cow, prior to attachment of the milking machine; this being the premilking udder hygiene method commonly used today in the dairy industry, hereafter referred to as the WASH method; and, (3) premilking cleaning of the teats with a spray of water using a water hose and wiping with hands, massaging each teat using a minimum of 3 to 4 vertical motions up and down the sides of the teat, and 1 or 2 horizontal motions across the teat ends, followed by drying the teats with separate paper towels for each cow, and then predipping with a 0.5 weight percent Iodophor teat dip left on the teats for 60 seconds, and final drying with individual paper towels for each cow, prior to attachment of the milking machine to the teats; this being referred to as the PREDIP method.

The composition of the gel applied to the teats of the group of cows treated in the GEL method is given as follows:

0.50% Iodophor (Teat-Kote TM, Babson Bros, Co.)
2.00% Liqui-Nox (A phosphate free detergent; a trademarked product of Alconox, Inc. of New York, N.Y.)
4.75% Glycerine
0.75% Carboxymethyl cellulose (Aldrich Chemical Company, Inc.)

The experimental gel had a pH of 5.25 and a freezing point of −4° C. Viscosity and shear analyses of the gel showed an apparent viscosity value between 12,000 and 60,000 Cp at 25° C. under normal shear stress. This range depended upon how fast the gel was mixed, moved, or pumped because both the apparent viscosity and rate of shear for this type of fluid vary with changing shear stress. The relationship between viscosity, spindle speed and shear stress: As spindle speed and shear stress increase, apparent viscosity decreases. Other properties of the gel obtained from this analyses were a flow behavior index of 0.2605 and average fluid consistency index of 556.14 dyne-sec/cm$^2$.

Milk samples were taken from each cow and analyzed for total bacteria count, preliminary incubation count, iodine concentration, somatic cell count, percent protein and percent fat. The test procedure followed is given generally as follows:

MILK AND TEAT SWAB SAMPLES

Individual cow milk and teat swab samples were collected from each cow once a week for eight weeks. Samples were immediately placed on ice and transported to the laboratory for microbiological work.

Aseptic collection procedure using sterilized syringes, plastic tubes, and plastic vials were used to obtain milk samples from weigh jars. Before drawing each sample, the milk was properly agitated and the spout on each weigh jar was disinfected with a cotton swab soaked in 95% ethanol. Samples were used to determine bacteria population in the milk.

Duplicate samples were also obtained in vials to determine milk constituents (fat and protein percentages, and SCC). A third set of samples was collected from each cow in sample bags (Nasco's Whirl-Pak TM) for iodine residue determination. Enough volume was collected to analyze each sample in duplicate. Samples for milk constituents and iodine analyses were obtained from the drain at the bottom of weigh jars following adequate agitation of milk.

Teat swabbing was done by making three complete circular motions with equal pressure over the teat end surface; only the right front teat of each cow was swabbed. Swabs were placed in sterile test tubes containing 5 ml rinse solution and transported in iced water to the laboratory. The rinse solution was a mixture of 0.85% NaCl, 0.1% Proteose-peptone, and 0.2% Sodium Thiosulfate. After the preparation of rinse solution, test tubes containing 5 ml of the solution were autoclaved for 15 minutes to achieve sterility. Microbiological Work All samples were plated on 3M Petrifilm TM in duplicates of two dilutions to obtain a bacteria count comparable to the Standard Plate Count (SPC). The SPC method is commonly used to estimate gross contamination or total microbial population of raw milk. A Preliminary Incubation (PI) count was also obtained from each sample in similar method with SPC. The PI method is an indicator of psychrotrophic bacteria or those organisms that grow rapidly at refrigeration temperatures (2° to 7° C.). An aliquot (about 10 ml) of each milk sample was transferred into a sterile vial and incubated at ±1° C. for 18 hours ±15 minutes. Psychrotrophic organisms are commonly found in soil, water, and improperly cleaned or sanitized milking equipment.

Two dilutions of 1:10 and 1:100 were used for both raw milk and PI samples. Teat swab rinses were diluted to 1:100 and 1:1000. The decision to use these dilution factors was based on pre-trial results conducted according to procedures described in Standard Methods for the Examination of Dairy Products (SMEDP). Dilutions studied ranged between 1:10 and 1:10$^6$.

Petrifilms TM were prepared and incubated according to the directions for use provided by the 3M Company (Medical Surgical Division, 3M Health Care, St. Paul, MN). The temperature of incubation was ±1° C. for 48±3 hours as directed by SMEDP. Bacterial colonies were also counted according to SMEDP directions using a Quebec colony counter (American Optical Corporation). Iodine Residue Duplicate samples of milk samples were analyzed for iodine content using an Orion Model 901 Microprocessor Ionalyzer. An Ionic Strength Adjustor (ISA) was used to adjust ionic strength of samples and standards, 5M NaNO$_3$. Reference filling solution was equitransferent filling solution of 4M KCl saturated with AgCl, and the concentration of the standard iodide solution was 0.1M NaI.

Electrode operation (or Slope) was checked, as recommended by the instruction manual, before analyzing samples. Electrodes were also polished with polishing strips whenever appropriate.

Iodine level in each sample was determined in parts per million (ppm) following directions provided by the instrument's instruction manual. the procedure steps followed included:

1) Measure 100 ml of diluted standard (0.5 ppm) in a 150 ml beaker. Then 2 ml of ISA were added and the solution stirred thoroughly.
2) Electrodes were rinsed with distilled water, blot dried and placed in the beaker. When a stable reading was obtained, the meter was adjusted to display the value of the standard.
3) Step 1) was repeated with diluted standard of higher concentration (1 ppm).
4) Step 2) was repeated to display the second value of the standard
5) Finally, milk samples were analyzed by measuring 100 ml of the sample into a 150 ml beaker and 2 ml of ISA were added. The sample was stirred thoroughly. Electrodes were rinsed, blot dried and placed into the sample. Iodine concentration was read from the meter display.

Electrodes were rinsed and blot dried between measurements, and each milk sample was analyzed in duplicate.

MILK CONSTITUENTS

Duplicate samples were taken to the Dairy Herd Improvement Laboratory (at the Louisiana Animal Breeders Coop, Baton Rouge, La.) for determination of Somatic Cell Count (SCC). This data was analyzed as an indication of milk quality and udder health. Milk fat and protein percentages were also determined from the samples.

Somatic Cell Count was determined using a Fossomatic TM Model 215 equipment (Foss Food Technology Inc., Eden Prairie, Minn). This instrument is an automated microscope. For each example, a mixture was made containing 2 ml of a dye (Ethidium Bromide), 0.2 ml milk sample, and 1.8 ml of buffer. The mixture was placed into a cup seated on a rotating table that was attached to an electronic stirrer. At stirring speed of 600 rpm, enough force was generated to thoroughly mix the solution and also cause lysis of the somatic cell. This enabled the dye to stain the cell's DNA. The entire mixture was then flushed through a microsyringe except 0.3 ml which was dispensed for 12 seconds from a nozzle to a highly polished wheel. The wheel passed under an electron microscope where a photo eye counted the cells. Figures were electronically transferred to a printer and readings were recorded in thousands of cells/ml.

Foss Electric Milko Scan TM Model 605 (Foss Food Technology Inc., Eden Prairie, Minn.) was the instrument used to determine fat and protein percentages. Potassium dichromate was used as a preservative in all samples. Up to 6 ml of preserved raw milk was required to go through two stages of homogenization. About 0.33 ml of homogenized milk was placed into a cuvette where an infrared light was shone through. Then a series of filters arranged on a wheel passed behind the cuvette at a given interval. Each filter allowed the passage of only one spectrum of light. Milk components (fat, protein, lactose, etc.) were each measured by a different spectrum.

Electronic circuitry of a digital analyzer converted the amount of light that passed through the cuvette to a milk fat and protein percent. Figures were finally sent to a printer and percentages were printed in two decimal places. All samples were analyzed in duplicates.

PATHOGEN IDENTIFICATION

Milk samples from all quarters of infected cows were sent to the Division of Bacteriology - Mycology, Clinical Diagnostic Services, LSU Veterinary Teaching Hospital and Clinics, for prompt identification of bacterial organisms present. Samples were collected on all new cases before treatment was administered.

This procedure consisted of four main steps: 1) milk sample was agitated for about two minutes to evenly mix the cream; 2) then 0.1 ml of the sample was immediately streaked on a medium of Blood Agar (Tryptose B.A. Base) and MaConkey Agar; 3) plates were incubated for 24 to 48 hours at 35° C.; and 4) identification of colony type by Gram Staining procedure.

Different methods and commercial kits were used to identify the colonies: i) conventional biochemicals and API 20E (API, Division of Sherwood Products, Plainview, N.Y.) were used to identify gram negative rods; ii) gram positive rods (Norcodia and Mycobacterium) were identified using Acid Fast Stain method. Corynobacterim and Bacillus can also be identified with this procedure; iii) to identify gram positive cocci, a catalase (Hydrogen Peroxide) was required. Rapid Mastitis Test TM (Immucell, Portland, ME.) and Staph Ident TM (API, Division of Sherwood Products, Plainview, N.Y.) were commercial kits used to identify Staphylococcal organisms. Both procedures required Hydrogen Peroxide as a catalase. Identification of Streptococcal pathogens was done with the Rapid Mastitis Test TM, Carbohydrate Fermentation (Phenol Red), Bile Esculin, and Camp Test.

PREMILKING UDDER PREPARATION TIME AND PARLOR THROUGHPUT

Premilking udder preparation time (preptime) was defined as period from the time a cow entered the milking stall to the time a cluster was completely attached. This measurement was taken for all treatments.

Parlor throughput information was collected to determine how many cows/hr were milked in each treatment for each of the three groups. This grouping criteria was used to reduce variation due to machine-on time between groups. Timing of each group started with the parlor entrance of the first cow, and ended with complete removal of last cluster. Each group was measured twice a day (a.m. and p.m.) for two days. Treatment was then changed and measurements began again following a two-day break. The purpose of the break period was to allow milkers to get used to the new treatment. Fresh and treated cows were excluded. Time and number of cows milked were averaged for each treatment, and a rate of cows milked/hr was determined.

STATISTICAL ANALYSES

All microorganism counts and SCC observations were log transformed and analyzed. Bacteria counts were recorded according to procedures provided by SMEDP. Variables were analyzed using least-squares and linear methods of the General Linear Model (GLM) procedure as described by Statistical Analysis System Method. The experimental design used was a Split-plot in time, adapted from Gill and Haps.

Statistical model was:

$$Y_{ijkl} = h + a_i + B(a)_{ji} + \S_k + a\S_{ik} + E_{ijkl}$$

where:
$Y_{ijkl}$ = an observation of a dependent variable
h = overall mean common to all observations
$a_i$ = effect due to $i^{th}$ treatment
$B(a)_{ji}$ = effect due to $j^{th}$ cow in $i^{th}$ treatment
$\S_k$ = effect due to $k^{th}$ week
$a\S_{ik}$ = interaction effect between $i^{th}$ treatment and $k^{th}$ week
$E_{jikl}$ = error term, assumed random $(O, 6^2_e)$.

Cow was a random effect and all other effects, except error were considered fixed. Calculation of least-square means and test of differences between selected means was done using the GLM procedure of SAS.

The test results of all of the data collected are summarized in the Table for treatments made in accordance with each of the three methods, viz., "GEL", "WASH" and "PREDIP", supra.

TABLE

Least squares means for response variables by pre-milking teat cleaning treatment.

| | TREATMENT | | |
|---|---|---|---|
| RESPONSE VARIABLE | GEL | WASH | PREDIP |
| Total bacteria count | 1,184[a] | 2,481[b] | 1,118[a] |
| Teat end swab count (n) | 10,388[a] | 28,558[b] | 9,205[a] |
| Preliminary incubation count (n) | 2,048[a] | 4,587[b] | 2,527[a] |
| Somatic cell count (n) | 113,411[c] | 152,354[d] | 174,434[d] |
| Morning milk yield (kg) | 11.9 | 12.1 | 11.9 |
| Afternoon milk yield (kg) | 11.1 | 11.1 | 10.9 |
| Daily total milk yield (kg) | 23.0 | 23.2 | 22.7 |
| Preparation time (sec) | 95[a] | 66[b] | 106[a] |
| Parlor throughput (cows/hr) | 55.14[c] | 51.59[d] | 43.95[c] |
| Iodine in milk (ppm) | .011[a] | .009[b] | .010[ab] |
| Fat percent (%) | 3.14 | 3.17 | 3.16 |
| Protein percent (%) | 2.88 | 2.87 | 2.84 |

[a,b]Means in the same row without common superscripts differ at the P < .05 level.
[c,d]Means in the same row without common superscripts differ at the P < .10 level.

These data show: Total bacteria counts in mil were 1,184,2,481 and 1,118 organisms/ml for GEL, WASH and PREDIP respectively. GEL and PREDIP total organism counts were significantly lower than WASH counts, but were not different from each other. Teat end swab counts were 10,388,28,558 and 9,205 organisms/ml for GEL, WASH and PREDIP, respectively. GEL and PREDIP teat end swab counts were significantly lower than WASH counts, but were not different from each other. Preliminary incubation counts were 2,048, 4,587 and 2,527 organisms/ml for GEL, WASH and PREDIP, respectively. Preliminary incubation counts for GEL and PREDIP were significantly lower than WASH counts, but did not differ from each other.

No differences due to treatment were found for percent protein, percent fat, a.m. milk yield, p.m. milk yield or daily total milk yield. Iodine in the GEL treatment was significantly different from WASH. The difference was .002 ppm with all three treatments being well within legal and acceptable limits. Somatic cell counts were significantly lower in the GEL treatment cows than in WASH or PREDIP.

Eight clinical cases of mastitis occurred during the trial with 5 in the WASH, 3 in the PREDIP and 0 in the GEL treatments, respectively. Organisms cultured from clinical cases in WASH cows included Streptococcus bovis, Streptococcus dysgalactiae, Staphylococcus aureus and Klebsiella sp. Cultured organisms in PREDIP cows included Escherichia coli with two cases being unidentified as to causative organism.

Preparation times for GEL, WASH and PREDIP were 95,66 and 106 seconds, respectively. Parlor throughputs were 55.14, 51.59 and 43.93 cows per hour for GEL, WASH and PREDIP treatments, respectively.

GEL and PREDIP treatments significantly improved milk quality and teat end contamination over the standard WASH. The GEL treatments resulted in more cows per hour milked and greater parlor efficiency. No clinical mastitis was observed in the GEL group during the experiment while 3 and 5 cases occurred in the PREDIP and WASH treatments, respectively. Somatic cell counts were lower in cows being cleaned with the GEL treatment. Iodine in milk was well within legal and acceptable levels for all three treatments.

It is clear that the GEL procedure, the method and composition of this invention, is superior to both the WASH and PREDIP procedures.

It is apparent that the composition and method of this invention can be varied to some extent without departing the spirit and scope thereof.

Having described the invention, what is claimed is:

1. A composition for improving teat and udder hygiene in preparing agricultural animals soiled with manure, mud and other dirt for machine milking which comprises
   an admixture of
   (a) water,
   (b) a germicide in concentration sufficient to destroy environmental bacteria that cause mastitis,
   (c) a soap, detergent, surfactant or combination thereof sufficient to provide good wetting and cleaning properties,
   (d) a skin softener and moisturizer for the protection of the skin surfaces of the teats and udder,
   (e) an aqueous gelling agent in concentration sufficient to gell with the water to form a tactile palpable jelly-like mass the apparent viscosity of which ranges from about 1,500 Cp to about 2,000,000 Cp, as measured at 25° with a Brookfield LVT Viscometer equipped with a helipath stand and using T-bar spindles A, B, C, D, E and F at rotational speeds up to 6 rpm, which can be applied to the teats and udder of the animals to soften the manure, mud and other dirt, destroy environmental bacteria that cause mastitis, and clean the teats and udder without the use of extraneous water, and without separation of a liquid phase from the admixture.

2. The composition of claim 1 wherein the apparent viscosity of the tactile palpable jelly-like mass ranges from about 3,000 Cp to about 150,000 Cp.

3. The composition of claim 1 wherein the germicide component of the composition is selected from the group consisting of salts of chlorhexadine, hypochlorites, iodine, peroxides and quaternary ammonium compounds.

4. The composition of claim 3 wherein the germicide component is present in the composition in concentration ranging from about 0.001 percent to about 4 percent, based on the total weight of the composition.

5. The composition of claim 3 wherein the germicide component is present in the composition in concentration ranging from about 0.10 percent to about 0.75 percent.

6. The composition of claim 1 wherein the aqueous gelling agent is a cellulose ether, polysaccharide, polyacrylamide or gelatin.

7. The composition of claim 6 wherein the aqueous gelling agent is present in the composition in concentration ranging to about 10 percent, based on the total weight of the composition.

8. The composition of claim 7 wherein the concentration of the aqueous gelling agent in the composition ranges from about 0.5 percent to about 5 percent.

9. The composition of claim 1 wherein the concentration of the soap, detergent, surfactant or combination thereof added for the reduction of surface tension of the water ranges from about 0.01 percent to about 5 percent, based on the total weight of the composition.

10. The composition of claim 9 wherein the concentration of the soap, detergent, surfactant or combination thereof added for the reduction of surface tension of the water ranges from about 2 percent to about 5 percent.

11. The composition of claim 1 wherein the skin softener and moisturizer is lanolin, glycerine or laurel sulfate.

12. The composition of claim 11 wherein the concentration of the skin softener and moisturizer in the composition ranges from about 0.01 percent to about 10 percent, based on the total weight of the composition.

13. The composition of claim 11 wherein the concentration of the skin softener and moisturizer in the composition ranges from about 0.1 percent to about 5 percent.

14. The composition of claim 1 wherein the composition further includes a color additive.

15. A method for preparing the teats and udder of an agricultural animal soiled with manure, mud and other dirt for machine milking, which comprises
   applying to each teat of the animal a composition comprising an admixture of (a) water, (b) a germicide in concentration sufficient to destroy environmental bacteria that cause mastitis, (c) a soap, detergent, surfactant or combination thereof sufficient to provide good wetting and cleaning properties, (d) a skin softener and moisturizer for the protection of the skin surfaces of the teats and udder, and (e) an aqueous gelling agent in concentration sufficient to gell with the water to form a tactile palpable jelly-like mass, the apparent viscosity of which ranges from about 1,500 Cp to about 2,000,000 Cp, as measured at 25° C. with a Brookfield LVT Viscometer equipped with a helipath stand and using T-bar spindles A, B, C, D, E and F at rotational speeds up to 6 rpm, allowing the composition to remain on each teat for a period sufficient to soften the manure, mud and other dirt and destroy environmental bacteria that cause mastitis, wiping and cleaning each teat without use of extraneous water to remove said composition, without separation of a water phase from the composition, and then attaching the milking machine to the cleaned teats of the animal.

16. The method of claim 15 wherein the apparent viscosity of the tactile palpable jelly-like mass ranges from about 3,000 Cp to about 150,000 Cp.

17. The method of claim 15 wherein the germicide component of the composition applied to each teat of the animal is selected from the group consisting of salts of chlorhexadine, hypochlorites, iodine, peroxides and quaternary ammonium compounds.

18. The method of claim 17 wherein the germicide component of the composition applied to each teat of the animal is present in the composition in concentration ranging from about 0.001 percent to about 4 percent, based on the total weight of the composition.

19. The method of claim 18 wherein the germicide component of the composition applied to each teat of the animal is present in the composition in concentration ranging from about 0.10 percent to about 0.75 percent.

20. The method of claim 15 wherein the aqueous gelling agent of the composition applied to each teat of the animal is a cellulose ether, polysaccharide, polyacrylamide or gelatin.

21. The method of claim 20 wherein the aqueous gelling agent of the composition applied to each teat of the animal is present in the composition in concentration ranging up to about 10 percent, based on the total weight of the composition.

22. The method of claim 21 wherein the aqueous gelling agent of the composition applied to each teat of the animal ranges from about 0.5 percent to about 5 percent.

23. The method of claim 15 wherein in the composition the concentration of the soap, detergent, surfactant, or combination thereof added for the reduction of surface tension of the water ranges from about 0.01 percent to about 5 percent, based on the total weight of the composition.

24. The method of claim 23 wherein in the composition the concentration of the soap, detergent, surfactant, or combination thereof added for the reduction of surface tension of the water ranges from about 2 percent to about 5 percent.

25. The method of claim 15 wherein in the composition the skin softener and moisturizer is lanolin, glycerine or laurel sulfate.

26. The method of claim 25 wherein the concentration of the skin softener and moisturizer in the composition ranges from about 0.01 percent to about 10 percent, based on the total weight of the composition.

27. The method of claim 25 wherein the concentration of the skin softener and moisturizer in the composition ranges from about 0.1 percent to about 5 percent.

28. The method of claim 15 wherein the composition further includes a color additive.

* * * * *